(12) United States Patent
Niichel

(10) Patent No.: US 8,518,448 B2
(45) Date of Patent: *Aug. 27, 2013

(54) SUSTAINED RELEASE BEADS AND SUSPENSIONS INCLUDING THE SAME FOR SUSTAINED DELIVERY OF ACTIVE INGREDIENTS

(76) Inventor: Robert Niichel, Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/089,097

(22) Filed: Apr. 18, 2011

(65) Prior Publication Data

US 2011/0195157 A1 Aug. 11, 2011

Related U.S. Application Data

(63) Continuation-in-part of application No. 12/492,995, filed on Jun. 26, 2009.

(51) Int. Cl.
*A61K 9/16* (2006.01)
*A61K 9/50* (2006.01)

(52) U.S. Cl.
CPC ........................................ *A61K 9/50* (2013.01)
USPC .............. 424/494; 424/439; 426/72; 426/74; 426/289; 426/590; 426/594

(58) Field of Classification Search
None
See application file for complete search history.

(56) References Cited

U.S. PATENT DOCUMENTS

| | | | | | |
|---|---|---|---|---|---|
| 4,182,778 | A | * | 1/1980 | Hall et al. | 426/72 |
| 5,510,119 | A | * | 4/1996 | Santus et al. | 424/490 |
| 2006/0068019 | A1 | * | 3/2006 | Dalziel et al. | 424/490 |
| 2006/0263427 | A1 | * | 11/2006 | Roberts et al. | 424/468 |
| 2006/0286259 | A1 | * | 12/2006 | Hargreaves | 426/590 |
| 2007/0238762 | A1 | * | 10/2007 | Lautt | 514/352 |
| 2008/0075784 | A1 | * | 3/2008 | Friesen et al. | 424/493 |

OTHER PUBLICATIONS

Kerrigan et al, "Fatal caffeine overdose: two case reports" Forensic Science International, 153 (2005), p. 67-69.*
Ballantyne, "Strange but true: drinking too much water can kill" Scientific American, Jun. 21, 2007, 29, p. 1-2.*
Fox et al "When caffeine kills: energy drinks under the spotlight" MSNBC, Oct. 23, 2012 (p. 1-6).*
"Theophylline" Wikipedia, retrieved online on Nov. 21, 2012, pp. 1-5.*
"Caffeine" Wikipedia, retrieved online on Nov. 27, 2012, (p. 1-20).*

* cited by examiner

*Primary Examiner* — Bethany Barham

(57) ABSTRACT

Sustained-released beads providing active ingredients over an extended period of time to an individual orally ingesting the sustained release beads. The sustained-release beads can be part of a suspension wherein the sustained-release beads are suspended and evenly dispersed in the suspension. Binding agents are used to form the structural framework of the sustained released beads and retain the active ingredients without chemical or electrical bonding. The components of the dispersion medium are GRAS designated, making the suspension suitable for use as a food product.

12 Claims, 3 Drawing Sheets

US 8,518,448 B2

SUSTAINED RELEASE BEADS AND SUSPENSIONS INCLUDING THE SAME FOR SUSTAINED DELIVERY OF ACTIVE INGREDIENTS

This application is a Continuation-In-Part application of U.S. application Ser. No. 12/492,995, filed Jun. 26, 2009, and which is hereby incorporated by reference in its entirety.

BACKGROUND

Individuals taking supplements and/or medications are often required to ingest capsules or pills multiple times per week, and in some instances, multiple times per day, in order to receive the necessary amount of the active ingredients contained therein at the appropriate time. Traditionally, this has required an individual to self-monitor their capsule or pill in-take, such as through the use of a medication log or a pill box having multiple labeled compartments. These methods include ample opportunity for human error. Furthermore, the requirement of having to take multiple pills per day or per week is cumbersome and inconvenient.

As an alternative, some medications and/or supplements have been provided in sustained-released pills. Sustained-released pills attempt to alleviate the burdens of taking numerous pills per day by providing relatively large amounts of medicine in a single pill that gradually releases the quantity of medicine, over an extended period of time once ingested. Generally speaking, pills of this type are limited to the delivery of medicines regulated by the U.S. Food and Drug Administration. Furthermore, the periods of time over which the medication is gradually released are relatively short, and almost always less than 24 hours. Accordingly, these pills do not resolve the issue where an individual is required to take multiple doses of a medication over several days, weeks or months.

Additionally, the options for sustained release of medication are believed to be mostly limited to pills or capsules. However, some individuals finds pills or the like difficult to deal with. For instances, pills are generally small and can easily be lost if dropped. Also, many individuals have difficulty swallowing pills, especially younger children.

One example of a sustained-release medicine in a non-capsule form is the composition described in U.S. Pat. No. 6,001,392. The composition generally includes drug/resin complexes that may be carried in a liquid composition, wherein the drug is an antitussive. The drug/resin complexes utilize cross-linked ion exchange resins, with the drug adsorbed on to the cross-linked ion exchange resin via ionic bonds between the drug and the ion-exchange resin. The manner of making drug/resin complexes using ion-exchange resins can be relatively complicated and expensive. Often, the ability to alter the period of time over which the medication is released is controlled by using substantial coating layers, rather than manipulating the drug/resin complex. For example, some drug/resin complexes of the '392 patent require coating layers that are 50% w/w drug in order to provide sustained release of the antitussive. The requirement for this relatively large amount of coating layer raises the overall price of manufacturing the drug/resin complexes.

The drug/resin complexes of the '392 patent may be carried by liquid compositions that generally include ingredients that are not deemed suitable for use in foods (either in any quantity of above certain quantities), such as polyethylene glycols (PEGS) and certain ion-exchange resins. For example, the '392 patent utilizes Amberlite IR-69 as the ion exchange resin, which does not carry a GRAS (Generally Regarded As Safe) designation from the U.S. Food and Drug Administration. Thus, while the '392 patent describes drinkable liquid compositions for sustained release of antitussives, the '392 patent is limited to medicinal applications that are regulated by the U.S. Food and Drug Administration.

SUMMARY

Disclosed are various embodiments of sustained-release beads including binding agents and active ingredients for oral ingestion by a mammal (e.g., a human) to thereby provide active ingredients to the mammal in a sustained-released fashion. The sustained-release beads may be included in a suspension wherein the sustained-release beads are evenly dispersed throughout the suspension. In one particular feature of the sustained-release beads, the binding agents are cellulose-based and the sustained-release beads do not have an external coating. In another embodiment, the sustained-release beads include only ingredients that are GRAS-compliant or present in GRAS-compliant quantities.

In one embodiment, a suspension includes a dispersion medium and a dispersed phase. The dispersion medium includes an aqueous solution and a pH modifier. The dispersed phase includes one or more sustained-release beads. The sustained-release beads include one or more binding agents and one or more active ingredients.

In another embodiment, a beverage includes a receptacle and a suspension contained within the receptacle. The suspension includes a dispersion medium and a dispersed phase. The dispersion medium includes an aqueous solution and a pH modifier. The dispersed phase includes one or more sustained-release beads. Each sustained-release bead includes one or more binding agents and one or more active ingredients. The beverage may be in the form of a sports drink that includes a fluid receptacle and a fluid suspension contained in the fluid receptacle. The fluid receptacle includes a base, a surrounding sidewall extending upwardly from the base to terminate in an open mouth, and a closure adapted to releasably cover the mouth. The suspension includes a dispersion medium and a dispersed phase. The dispersion medium includes an aqueous solution and a pH modifier. The dispersed phase includes one or more sustained-release beads. Each sustained-release bead includes one or more binding agents and one or more active ingredients.

In another embodiment, a method for producing an orally ingestible fluid includes providing one or more sustained-release beads, providing a dispersion medium, and mixing the one or more sustained-release beads in the dispersion medium. The sustained-release beads include one or more binding agents and one or more active ingredients. The one or more binding agents may be provided from 40 wt % to 95 wt % of the sustained-release bead. The one or more active ingredients may provide from 5 wt % to 60 wt % the sustained-release bead. The dispersion medium includes an aqueous or organic solution and a pH modifier.

It is to be understood that the foregoing is a brief summary of various aspects of some disclosed embodiments. The scope of the disclosure need not therefore include all such aspects or address or solve, all issues noted in the background above. In addition, there are other aspects of the disclosed embodiments that will become apparent as the specification proceeds.

The foregoing and other features, utilities, and advantages of the subject matter described herein will be apparent from the following more particular description of certain embodiments as illustrated in the accompanying drawings. In this regard, it is to be understood that the scope of the invention is to be determined by the claims as issued and not by whether given subject includes any or all features, or, aspects noted in this Summary or addresses any issues noted in the Background.

BRIEF DESCRIPTION OF THE DRAWINGS

The preferred and other embodiments are disclosed in association with the accompanying drawings in which.

DETAILED DESCRIPTION

Figure 1:
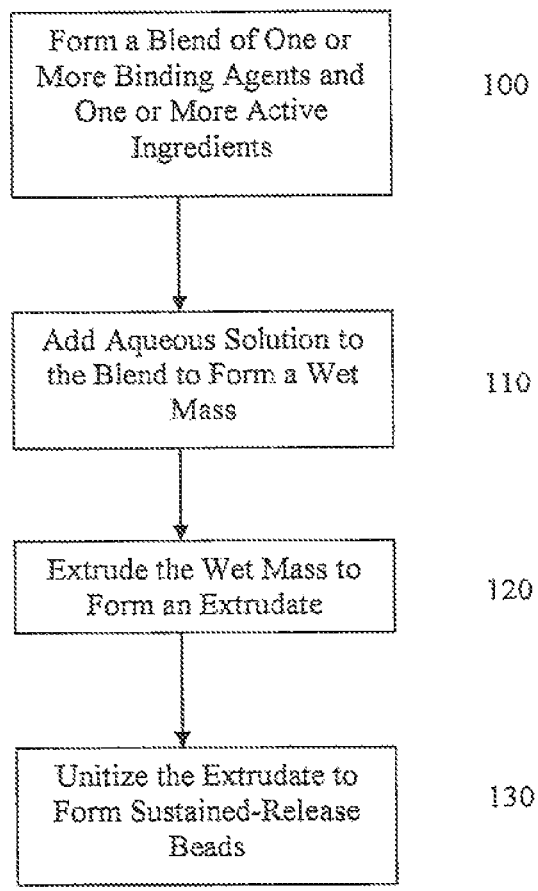
FIG. 1 is a flow chart depicting a method for making sustained-release beads as disclosed herein.

In a first embodiment, active ingredients may be provided to a mammal, such as a human, in a sustained-released manner through the use of a suspension that is orally ingested by the mammal. The suspension generally includes a dispersion medium and a dispersed phase, wherein the dispersed phase includes a plurality of sustained-release beads suspended in the dispersion medium. The sustained-release beads may include one or more active ingredients and are configured in such a way as to release the active ingredients over a period time rather than all at once. The dispersion medium is generally a fluid, such as a liquid or a gel, while the sustained-release beads of the dispersed phase are generally solid. Because of the nature of the suspension, the sustained-release beads remain suspended in the fluid dispersion medium and do not dissolve in the dispersion medium.

The dispersion medium, includes an aqueous solution. Any suitable aqueous solution may be used, such as water, milk, fruit, juice, alcohol, or the like. Organic solutions may also be used for the dispersion medium. The aqueous solution is preferably non-toxic or used in a non-toxic amount. In one embodiment, the aqueous solution may account for from 75 wt % to about 99.5 wt % of the dispersion medium.

The dispersion medium also includes one or more pH modifiers for modifying the pH of the dispersion medium. The pH of the dispersion medium may need to be adjusted with the pH modifier in order to provide a medium that will not degrade the sustained-release beads dispersed therein at too fast a rate. For example, when the aqueous solution of the dispersion medium is water having a pH of from between 6 and 8.5, the sustained release beads cannot be dispersed with the dispersion medium and stored for any prolonged period of time due to the rate at which the sustained release beads will degrade in the water. Accordingly, in some embodiments, it may be necessary to adjust the pH of the dispersion medium to within a range of 2.0 to 5.5 to help ensure the sustained-release beads will not degrade at too fast a rate when dispersed in the dispersion medium. For sport nutrition/enhanced water products, the pH of the dispersion medium can be adjusted to within the range of 2.0 to 3.5. For protein shakes, yogurts, and the like, the pH of the dispersion medium can be adjusted to within the range of 4.0 to 5.0.

Any pH modifier suitable for use in consumable products, such as the beverages described herein, can be used in the dispersion medium. Exemplary pH modifiers include, but are not limited to citric acid, phosphoric acid, sodium citrate, potassium citrate, ascorbic acid, benzoic acid, malic acid, lactic acid, fumaric acid, and combinations thereof.

The amount of pH modifier included in the dispersion medium will generally be based on how much pH modifier is needed to alter the pH to within the suitable range of from 2 to 5.5 and which still provides a suspension that is safe for humans to consume. In some embodiments, pH modifier can be added to, the suspension until the desired pH is obtained. As an example, for water with a pH of 7.0, a pH modifier including 20 mM citric acid and 5 mM sodium citrate can reduce the pH of the water to 3.0.

In some embodiments, the dispersion medium also includes one or more thickening agents. Any suitable thickening agent may be used for the dispersion medium. In one embodiment, the thickening agent is non-toxic or used in a non-toxic quantity so that the suspension is safely ingestible. Suitable thickening agents include, but are not limited to, agar agar, xanthan gum, guar gum, gelatin, acacia gum, pectin, ester gum, Arabic gum, and gullan gum. The amount of the one or more thickening agents in the dispersion medium is not limited and may be adjusted to arrive at any desired viscosity for the dispersion medium. In one embodiment, the total amount of the one or more thickening agents in the dispersion medium ranges from 0.05 wt % to 2 wt % of the dispersion medium. In another embodiment, a quantity of one or more thickening agents is added to the aqueous solution until the dispersion medium has a viscosity in the range of from about 0.894 cP to about 250,000 cP.

As noted above, one aim of including the one or more thickening agents in the dispersion medium is to increase the viscosity of the dispersion medium. By increasing the viscosity of the dispersion medium through the addition of thickening agents, the dispersed phase of the suspension will be suspended throughout the dispersion medium, even after periods of time during which settling might occur. When the beads of the dispersed phase are evenly suspended throughout the dispersion medium, a generally consistent number of beads will be provided with each portion of the suspension ingested.

Additional components may also be included in the dispersion medium, such as components to further alter the consistency, appearance, taste, smell, or shelf life of the dispersion medium. In one embodiment, simple syrup is included in the dispersion medium. Any amount of simple syrup may be added. In one embodiment, simple syrup is added to the dispersion medium at a rate of 1 part simple syrup for every 5 parts aqueous solution. Sweetener may also be added to the dispersion medium. The type, of sweetener added to the dispersion medium is not limited and may include natural and synthetic sweeteners. In one embodiment, the sweetener added to the dispersion medium is sugar, such as fructose, sucrose or ribose. In another embodiment, sweetener is excluded or a diet sweetener is used in order to make a diet dispersion medium. When sweetener is used, it may be added in any suitable amount to alter the taste of dispersion medium. Any suitable type and amount of preservatives may also be added to the dispersion medium. Additionally, any suitable type and amount of fragrance may be added to the dispersion medium. Furthermore, any suitable type and amount of coloring may be added to the dispersion medium.

In another embodiment, the dispersion medium is GRAS-compliant. GRAS status is an American Food and Drug Administration (FDA) designation that a chemical or substance added to food is considered safe by experts, and so is exempted from the usual Federal Food, Drug, and Cosmetic Act (FFDCA) food additive tolerance requirements. Most GRAS substances have no quantitative restrictions as to use, but some GRAS substances do have a quantitative limit for use in food. A GRAS-compliant dispersion medium may include a dispersion medium having only ingredients with a GRAS designation. For example, the dispersion medium may contain a limited amount of polyethylene glycols (PEGs) because PEGs are GRAS substances that have a quantitative limit for use in food.

The dispersed phase of the suspension generally includes one or more sustained-release beads. As noted above, the sustained-release beads are generally solid and do not dissolve in the dispersion medium. When the dispersion medium has a suitable viscosity, the sustained-release beads are suspended in the dispersion medium. In one embodiment, the sustained-release beads are uniformly dispersed throughout the dispersion medium. In another embodiment, the sustained-release beads can be settled at the bottom of a dispersion medium and then dispersed by shaking the dispersion medium.

The sustained-release beads include one or more binding agents and one or more active ingredients. The binding agents and active ingredients are generally processed in such a way that both components are evenly distributed throughout the sustained-release bead. The binding agents serve to retain the shape of the sustained-release beads while maintaining the active ingredients in the sustained-release beads. Preferably, there are no chemical or electrical (e.g., ion sharing) reactions between the binding agents and the active ingredients. Rather, the sustained-release beads are held together and the active ingredients are retained within the sustained-release beads by the structural framework provided by the binding agents during processing of the beads.

Any suitable amount of each binding agent may be used in the sustained-release beads. In one embodiment, the total amount of binding agents in the sustained-release beads may range from 40 wt % to 95 wt % of the sustained-release beads. In another embodiment, the total amount of binding agents in the sustained-release beads is approximately 50 wt % of the sustained-release beads. The amount of binding agent included in each sustained-release bead may be adjusted in order to alter the sustained-release of the active ingredient once the suspension is ingested. Generally speaking, higher binding agent concentration in the sustained-release beads will result in a slower sustained-release of the active ingredient. The dispersed phase may include beads having different binding agent concentrations such that the sustained-release beads release the active ingredients at varying time intervals, providing for sustained release of active ingredients over an extend period of time.

Any number of different binding agents may be used in the sustained-release beads. In one embodiment, the binding agents are non-toxic or are used in non-toxic amounts. Exemplary binding agents include, but are not limited to, methyl cellulose, ethyl cellulose, microcrystalline cellulose, croscarmellose sodium, dicalcium phosphate, cellulose, hypromellose, hydroxypropyl methylcellulose, carboxymethylcellulose, and hydroxyethyl cellulose. In one embodiment, only cellulose-based binding agents are used.

The amount of each active ingredient in the sustained-release beads is not limited. In one embodiment, the total amount of active ingredients in the sustained-release beads may range from 5 wt % to 60 wt % of the sustained-release beads. In another embodiment, the total amount of active ingredients in the sustained-release beads is approximately 50 wt % of the sustained-release beads. The concentration of active ingredients, the number of active ingredients and the type of active ingredients may vary amongst the various sustained-release beads used in the suspension.

Any number of different active ingredients may be used in the sustained-release beads. Active ingredients may generally include any type of element, compound, or combination or derivative therefore that may be administered to a mammal to effect a beneficial change in the mammal's physical or mental state. In one embodiment, the class of active ingredients are those elements or compounds for aiding a mammal during exercise. Exemplary active ingredients of this class include electrolytes, such as potassium, magnesium, sodium, and calcium, and stimulants, such as caffeine. Active ingredients may also include vitamins and minerals. Active ingredients may also include amino acids. Other classes of active ingredients include, but are not limited to, those to fight disease, those to prevent disease, those to alleviate or relieve pain, those to improve bone and joint health, those to improve mental concentration and alertness, those to improve physical appearance, and those to combat mental illness. In one embodiment, the active ingredients are materials having a GRAS designation. The active ingredients can include materials that are available over the counter or by prescription only.

Exemplary active ingredients suitable for use in sustained-release beads dispersed in foods and beverages used in fitness and sports applications (e.g., enhanced water beverages), include vitamins A, B1, B2, B3, B5, B6, B7, B9, B12, C, D, E H, K; glucosamine; chondroitin; minerals such as potassium, calcium, sodium, magnesium, iron, phosphorous, manganese, zinc, iodine, selenium, copper, chromium, chloride, fluoride, molybdenum, and sulfur; stimulants such as caffeine, ginseng, ginko, green tea, citicloline, and yohimbe; relaxants such as melatonin, serotonin, inositol, 5-HIP (5-hydroxytryptophan); probiotics such as *LACTOBACILLUS (L.) acidophilus, L. brevis, L. bulgaricus, L. casei, L. GG, L. plantarum, L. salivarius, STREPTOCOCCUS thermophilus, BIFIDOBACTERIUM (B.) bifidum, B. infantis, B. longum*, and *ENTERODOCCUS faecium*; and amino acids, including isoleucine, alanine, selenocysteine, leucine, asparagine, serine, lysine, aspartic acid, tyrosine, methionine, cysteine, arginine, phenylalanine, glutamic acid, histidine, theronine, glutamine, ornithine, tryptophan, glycine, taurine, valine, and proline.

Exemplary active ingredients suitable for use in sustained release beads and which are available over the counter include aspirin, acetaminophen, ibuprofen, naproxen, Doxylamine, Dextromethorphan, Loratadine, Pseudophedrine, Phenylephrine, Diphenhydramine, Chlorpheniramine maleate, and Guaifenesin.

The sustained-release beads of the dispersed phase may include a coating layer to further alter the rate of sustained-release of the active ingredients. Additional coating layers will generally result in a slower sustained-release of the active ingredients. In one embodiment, the coating layer for the sustained-release beads is a cellulose-based coating layer, such as an ethyl cellulose based coating layer. In one embodiment, the coating layer is a SURELEASE® coating layer as manufactured by Colorcon of West Point, Pa. The coating may be added in any amount to the sustained-release beads. In one embodiment, the coating is added at less than about 15 wt % of the sustained-release bead.

As with the dispersion medium, the sustained-release beads of the dispersed phase may include additional components to alter the consistency, appearance, taste, smell, or shelf life of the sustained-release beads. These components may be added as either additional ingredients in the sustained-release beads or as coating layers on the sustained-release beads. In one embodiment, a coloring agent is used to alter the color of the sustained-release beads. The sustained-release beads may be colored by mixing dyes with the active ingredients and binding agents during the formation of the sustained-release beads. The sustained-release beads may also be colored by coating the sustained-release beads with a liquid dye mixture (e.g., OPADRY® coating as manufactured by Colorcon of West Point, Pa.). Coating the sustained-release beads with a liquid dye mixture may be followed by adding a transparent coating to the sustained-release beads. The sustained-release beads may also be colored by using metallic translucent colorings that may be applied during the manufacture of the sustained-release beads or as a coating to the sustained-release beads.

The size and shape of the sustained-release beads are also not limited. The shape of the sustained-release beads may include spheres, cubes, and rods as well as any type of irregular shape. In one embodiment, the size of the sustained-release beads is such that the sustained-release beads may be seen in the suspension without need for magnification, but also such that the sustained-release beads are not substantially felt in the mouth or throat when being orally ingested. One suitable range for the diameter of the sustained-release beads is less than 5.0 mm, such as from 0.5 mm to 5.0 mm. The sustained-release beads may also be much smaller, such as on a micrometer or nanometer scale.

Once the sustained-release beads are orally ingested by a mammal, the sustained-release beads will generally travel to a location in the digestive tract where conditions begin to break down the sustained-release beads. The conditions that break down the sustained release beads can include any of the chemical components in the stomach or gastrointestinal tract, including acidic and basic conditions. The rate at which the conditions are able to break down the sustained-release is bead is controlled by the type and amount of binding agent used in the sustained-release beads, including any coatings applied to the sustained-release beads. Sustained-release beads with relatively minor amounts of binding agents will be, broken down quickly in the digestive tract. Once broken down, the active ingredients in the sustained-release beads become available to be taken up by the circulatory system of the mammal. Sustained-release beads with higher amounts of binding agents and coatings will break down relatively slowing, meaning that the active ingredients will not become available, to be taken up by the circulatory system until after a longer period of time. In this manner, active ingredients may be provided to a mammal over a sustained period of time when sustained-release beads with varying binding agent concentrations and coatings are included in the suspension orally ingested by a mammal.

In another embodiment, a method for making sustained-release beads such as the sustained-release beads described above and used in the dispersed phase of the suspension described above includes the extruding and unitizing of a mixture of binding agents and active ingredients. As shown in FIG. 1, the method includes forming at 100 a blend of one or more binding agents and one or more active ingredients, adding aqueous solution to the to the blend at 110 to form a wet mass, extruding the wet mass at 120, and unitizing the extrudate at 130 to form sustained-release beads.

Blending together of the one or more active ingredients and the one or more binding agents can be carried out according to any suitable method for blending two or more materials. In one embodiment, the one or more active ingredients and the one or more binding agents are in a powder form and are therefore blended by any known method for the blending together of various powders. Blending can be carried out for any suitable period of time and at any blending speed or rate. In one embodiment, the blending is carried out for 3 minutes in a low shear planetary mixer.

The initial amount of active ingredients and binding agents are not limited and, in one embodiment, may generally be in accordance with the weight ranges described above in the description of the sustained-release beads of the dispersed phase. In this respect, the total amount of active, ingredients may be from 5 wt % to 60 wt % of the blend and the total amount of the binding agent may be from 40 wt % to 95 wt % of the blend. The total amount of active ingredients may include one or more different active ingredients in any distribution and the total amount of binding agents may include one or more binding agents in any distribution. The active ingredients and binding agents suitable for use in the manufacture of the sustained-release beads are identical to the active ingredients and binding agents described in greater detail in the previous embodiments.

Additional components as described in greater detail above can also be blended together with the binding agents and the active ingredients in order to alter various characteristics of the beads resulting from extruding and unitizing the blend.

Once the blend is formed, aqueous solution is added to the blend to create a wet mass. Aqueous solution can be added to the blend in any suitable manner to create the wet mass. In one embodiment, the aqueous solution and blend are mixed in order to ensure sufficient wetting of the blend and creation of an evenly wet mass of materials. The aqueous solution is added to the blend at a solution to blend ratio of from 0.1:1.0 to 1:1. In one embodiment, the ratio is 0.35:1.0. Preferably, the aqueous solution is water.

The wet mass is then passed through an extruder in order to form an extrudate. Any suitable extruder may be used to extrude the wet mass. Suitable extruders include screw extruders, screen extruders, gear extruders, cylinder extruders and radial extruders. The operating conditions for the extruder are not limited and may be adjusted according to the user's requirements. The die for the extruder should generally be of a size approximate the desired cross sectional size for the beads. Due to the pressure and heat that may be applied to the wet mass during extrusion, the extrusion process generally results in the hardening of the binding agent to create the structural framework for the sustained-release bead and that maintains the active ingredient evenly dispersed throughout the sustained-release bead.

Extrudate is then unitized in order to form individual sustained-release beads. While having an appropriate cross-sectional size, the extrudate is typically of a length greater than desired for the individual sustained-release beads. Unitizing includes any process by which the extrudate is broken down into smaller units that fall within the desired size dimensions for the sustained-release beads. For example, if the extrudate is generally in the form of a long, cylindrical rod, the rod may be cut along its length as part of the unitizing process to create smaller rod-shaped sustained-release beads of the desired dimensions. Any unitizing method may be utilized in order to alter the extrudate into the desired shape for the sustained-release beads. In one embodiment where spherical sustained-release beads are desired, the extrudate may be sent to a spheronizer. Any suitable spheronizer and any suitable operating conditions for the spheronizer may be used.

Once unitizing is completed, the sustained-release beads may undergo further processing to refine, the sustained-release beads. One such process includes drying the sustained-release beads in order to remove a substantial portion of the moisture still included in the sustained-release: beads. In one embodiment, 85% or more of the moisture content of the sustained-release beads is removed by drying. Any suitable method of drying may be used in order to remove the aqueous solution content from the sustained-release beads. In another additional processing step, the beads may be coated to further adjust the sustained-release of the sustained-release beads. In one embodiment, the coatings are cellulose-based coatings, such as an ethyl cellulose-based coating. The addition of a coating will generally result in a slower sustained-release of the active ingredients than if the sustained-release bead does not include a coating. As discussed in greater detail above, additional coatings may also be added in order to change the color of the sustained-release beads.

In another embodiment, a beverage includes the suspension described in greater detail above. The beverage provides the active ingredients of the sustained-release beads to a mammal that orally ingests the beverage. The beverage generally includes a receptacle in which the suspension is contained. A receptacle of any size, shape and material that is capable of containing the suspension may be used. In one embodiment, the size of the receptacle is such that a single serving (e.g., 16.9 fl. oz.) can be contained in the receptacle. The receptacle may also be configured so as to be easily gripped by one hand or fit in a beverage holder of an automobile. The receptacle may be made form recyclable or non-recyclable material. The receptacle may include labeling or other indications of source and contents. The receptacle may also include a removable cap to secure the suspension, in the receptacle when the suspension is not being ingested. The suspension contained in the receptacle is identical to the suspension described in previous embodiments.

In another embodiment, packetized sustained-release beads are provided for easy transport of sustained-release beads and addition of sustained-release beads to any suitable fluid. The packetized sustained-release beads generally include a packet and a selected quantity of sustained-release beads contained in the packet.

The packet may be any suitable type of packet for containing the sustained-release beads. The packet may have any suitable size and shape and may be made of any suitable material. In one embodiment, the packet is of a size suitable for containing a single serving of sustained-release beads. The shape of the packet may be such that the depth of the packet is small relative to the length and width of the packet. In this manner, the packet has a generally flat shape and provides enhanced portability. The material of the packet may be any suitable material capable of containing the sustained-release beads. Such material may be recyclable or non-recyclable. In one embodiment, the material of the packet is paper, which allows for the packet to be torn open for access to the sustained-release beads contained therein. The packet may have, other opening means; such as perforations, seals, adhesives, zippers, and ties.

The sustained-release beads contained in the packet are identical or similar to the beads described above in a previous embodiment. The selected quantity of beads contained in the packet is, not limited. As noted above, in one embodiment the selected quantity may be a single serving of sustained-release beads. In this embodiment, the entire contents of the packet may be emptied into a suitable receptacle containing a dispersion medium for creating a beverage as described in a previous embodiment. The amount of sustained-release beads that constitute a single serving may vary depending on a variety of factors, including the mammal consuming the beads, the desired period of sustained-release, and type and amount of active ingredients included in the sustained-release beads.

Figure 2:
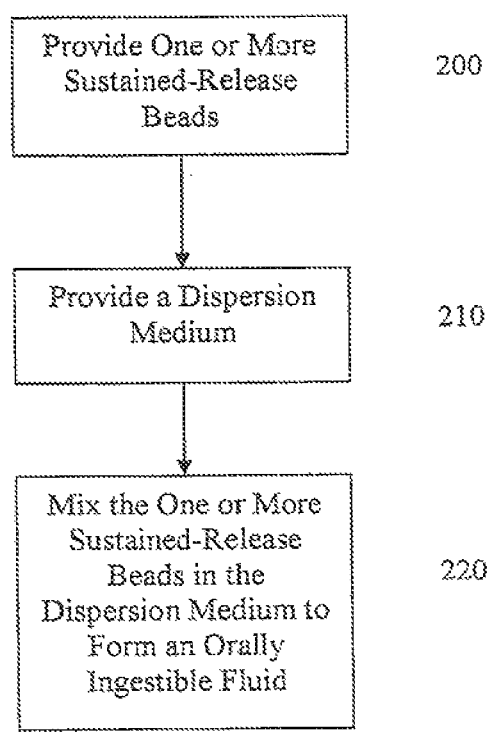
FIG. 2 is a flow chart depicting a method for making an orally ingestible fluid as disclosed herein.

In another embodiment, a method for producing an orally ingestible fluid is provided. As shown in FIG. 2, the method includes providing one or more sustained-release beads at 200, providing a dispersion medium at 210, and mixing the one or more sustained-release beads in the dispersion medium at 220. The resulting orally ingestible fluid may be ingested by a mammal to thereby provide the sustained-release beads in the digestive tract of the mammal. In the digestive tract, the sustained-release beads begin to break down due to the presence of various chemical components in the digestive tract. The rate at which the digestive tract breaks down the sustained-release beads is controlled by the amount of binding agent included in the sustained-release beads. Higher amounts of binding agents in the sustained-release beads, including coatings, will generally result in a slower break down of the beads. Once the beads are sufficiently broken down, the active ingredients become available to be taken up by the circulatory system of the mammal.

The one or more sustained-release beads provided in one step of the method are identical or similar to the sustained-release beads described in the previous embodiments. The dispersion medium provided in another step of the method is identical or similar to the dispersion medium described in previous embodiments.

The dispersion medium and the sustained-release beads are then mixed together in order to produce the orally ingestible fluid. Any manner of mixing the dispersion medium and the sustained-release beads together may be used, including pouring the sustained-release beads into the dispersion medium or vice versa. Additionally, any ratio of dispersion medium and sustained-release beads may be used. In one embodiment, the mixing of the dispersion medium and the sustained-release beads is conducted such that the sustained-release beads are suspended in the dispersion medium and evenly distributed throughout the dispersion medium.

The orally ingestible fluid may be customizable based on a specific order placed by a customer. More specifically, various sustained-release beads having various active ingredients may be provided and mixed with the dispersion medium to provide a fluid that specifically addresses the needs of a customer. For example, where a customer desires an orally ingestible fluid capable of providing stimulation and energy, the sustained-release beads mixed with the dispersion medium may have a relatively large amount of caffeine or, other stimulants.

In one embodiment, specialized orally ingestible fluids may be prepared by an automated assembly line. Receptacles for containing the orally ingestible fluid may be moved along a suitable transportation device, such as a conveyor belt, and under various dispensers containing sustained-release beads with varying compositions. As the receptacle moves along the conveyor belt and under the various dispensers, the dispensers may dispense or not dispense sustained-release beads into the receptacles based on the order of the customer and a computer program providing information to the dispensers regarding when to dispense sustained-release beads and when not to dispense sustained-release beads. The dispensers can also operate in accordance with computer programming instructions to vary how much of each type of sustained-release bead to dispense into the receptacle. The receptacles passing under the dispensers may already contain the dispersion medium, or the dispersion medium may be added after the sustained-release beads have been dispenses in the receptacles. The assembly line may also include mechanisms for shaking the receptacles after both dispersion medium and the specifically ordered sustained-release beads have been dispensed therein in order to evenly distribute the sustained-release beads throughout the dispersion medium.

An ordering system is also contemplated, wherein a customer may remotely place orders for specialized orally ingestible fluids or components of the orally ingestible fluids. In one embodiment, the ordering system includes the ability to order various sustained-release beads to suit the specific needs of the customer. For example, customers desiring sustained-release beads including active ingredients that can assist a consumer during periods of exercise may order sustained-release beads including electrolytes and stimulants. Customer may also include medical professionals who place orders for sustained-release beads that meet the health needs of their patients. Such system may include the ability to order over the telephone, via the Internet or through the mail.

In embodiments where sustained-release beads are ordered by a customer, the ordering method may further include receipt of the sustained-release beads ordered by the customer, and mixing the sustained-release beads with an appropriate dispersion medium to create an orally ingestible fluid. The appropriate dispersion medium may be obtained by the customer separately from the sustained-release beads. The beads may be mixed with the dispersion medium in any suitable manner, and in one embodiment, the beads are added to the dispersion medium followed by shaking the dispersion medium to disperse the beads throughout the dispersion medium.

Sustained-release beads received by a customer may also be dispensed in other non-solid food products. For example, sustained-release beads may be poured into a yogurt, shake or meal replacement beverage and stirred amongst the food. Consequently, consumption of the food product will provide the active ingredients of the sustained-release beads to the individual consuming the food product. Other non-solid foods into which the sustained-release beads can be added include, but are not limited to, baby food, compotes, jams, soups, and smoothies.

In another embodiment, a sports drink includes sustained-release beads having one or more active ingredients that tend to be depleted in a mammal during or after periods of exercise or that aid a mammal when preparing for, engaging in, or recovering from exercise. Accordingly, the sports drink may be orally ingested by a mammal before, during or after periods of exercise in order to provide the one or more active ingredients to the mammal undertaking the exercise.

The sports drink generally includes a fluid receptacle and a suspension. The fluid receptacle contains the suspension and generally includes a base, a surrounding sidewall extending upwardly from the base to terminate in an open mouth, and a closure adapted to releasably cover the open mouth. The suspension is identical to the suspension described in greater detail above, and generally includes a dispersion medium and a dispersed phase of one or more sustained-release beads.

Figure 3:
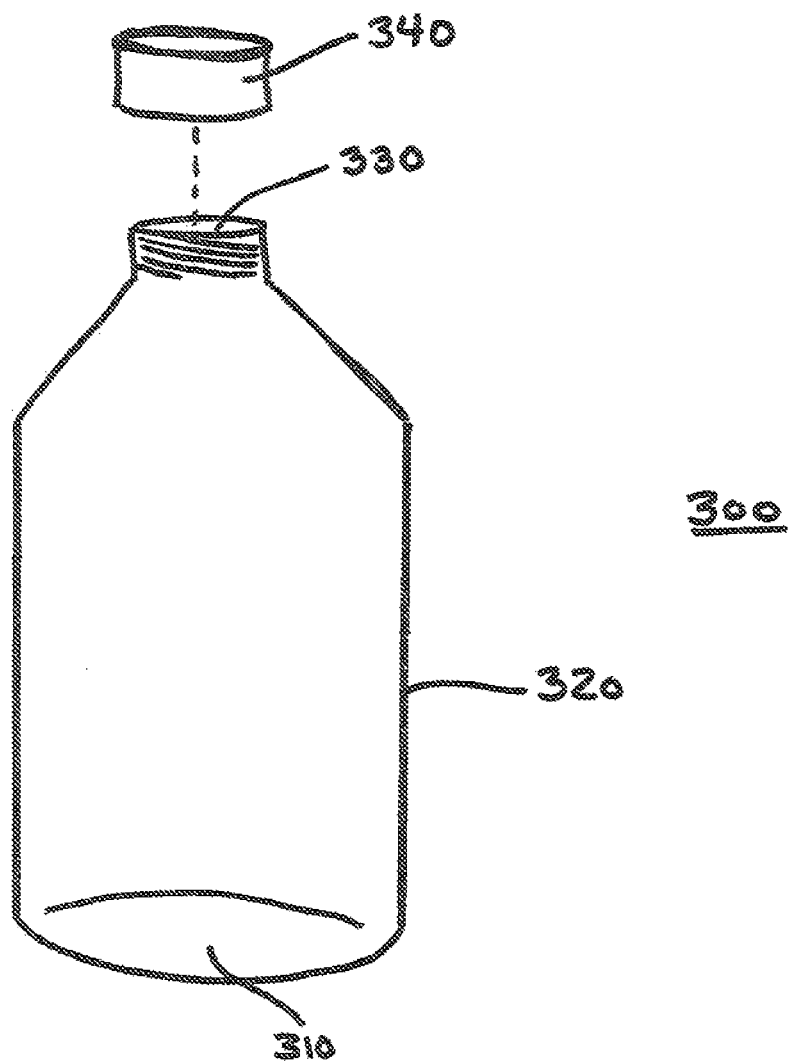
FIG. 3 is a perspective view of a sports drink as disclosed herein.

The fluid receptacle of the sports drink is illustrated in FIG. 3. The fluid receptacle 300 includes a base 310, a surrounding sidewall 320 extending upwardly from the base 310 to terminate in an open mouth 330, and a closure 340 adapted to releasably cover the open mouth 330.

As shown in FIG. 3, the fluid receptacle 300 has a generally cylindrical shape, including a circular base 310 and a surrounding sidewall 320 that is generally perpendicular to the circular base 310. However, the fluid receptacle 300 may have any suitable shape. The base 310 may be any shape and the surrounding sidewall 320 may be non-perpendicular to the base 310. The surrounding sidewall 320 may also be curved and contoured, rather than straight and flat as shown in FIG. 3. To this end, both the fluid receptacle 300 and the closure 340 can assume any of a variety of known or hereinafter developed configurations for accommodating the contents thereof.

As also shown in FIG. 3, the sidewall 320 tapers at the end opposite the base. 310 to terminate at an open mouth 330. The sidewall 320 need not taper as shown in FIG. 3, and may also flare outwardly. The size and shape of the open mouth 330 are not limited. The open mouth 330 generally provides access to the interior of the fluid receptacle 300 as bound by the base 310 and sidewall 320.

FIG. 3 further illustrates a closure 340. The closure 340 can be adapted to releasably cover the open mouth 330. The size and shape of the closure 340 are not limited. In one embodiment, the closure 340 has a similar shape and size as the open mouth 330. The closure 340 may releasably engage the open mouth 330 in any suitable manner. In one embodiment, the closure 340 engages the open mouth 330 in a fluid-tight seal so as to prevent fluid contained within the receptacle 300 from escaping the receptacle 300 via the open mouth 330. Exemplary manners for the closure 340 to releasably engage the open mouth 330 include, but are not limited to, an interference fit between the open mouth 330 and the closure 340 and a male and female thread system for screwing and unscrewing the closure 340 on and off the open mouth 330. In The closure 340 may also take the form of a material that covers the open mouth 330 and may be punctured to access the interior of the receptacle 300.

The overall size of the receptacle 300 is not limited. The size of receptacle may be suitable for containing a single serving of the suspension or may be large enough to include multiple servings of the suspension.

The materials of the receptacle 300 are not limited. In one embodiment, the materials of the receptacle 300 are fluid-impermeable so as to contain the suspension therein without leaks. The materials may be recyclable or non-recyclable. The receptacle 300 may also include indicia of source or contents, such as labels affixed to the exterior of the sidewall 320.

The suspension contained in the receptacle 300 is identical or similar to the suspension described in greater detail above, but specifically includes sustained-release beads having active ingredients of the type that tend to be depleted by a mammal during or after exercise or that aid a mammal when preparing for, engaging in, or recovering from exercise. Exemplary active ingredients for the sustained-release beads include electrolytes, such as potassium, magnesium, sodium, and calcium, stimulants, such as caffeine, and vitamins and minerals, such as vitamins B1, B2, B3, B5, B6 and B12.

Any suitable amount of the binding agents and active ingredients can be used for the sustained-release beads. In one embodiment, the total amount of the binding agents in the sustained-release beads is from 40 wt % to 95 wt % of the sustained-release beads and the total amount of the active ingredients in the sustained-release beads is from 5 wt % to 60 wt % of the sustained-release beads. In one embodiment, the suspension includes a variety of sustained-release beads having different compositions. The composition of the sustained-release beads may vary in both the type and amount of active ingredients and the type and amount of the binding agents. In this manner, the sports drink may provide various types and amounts of active ingredients to the mammal at various times. For example, the sports drink may include a first set of sustained-release beads including caffeine with relatively small amounts of binding agent and a second set of sustained-release beads including electrolytes with relatively large amounts of binding agent. When ingesting the sports drink having these types of sustained-release beads, the mammal will be provided with caffeine shortly after ingestion of the sports drink to help provide energy at the start of the period of exercise and then will be provided with electrolytes after a period of time during which electrolytes in the mammals body may have been depleted by the exercise. In another example, the sports drink includes various sustained-release beads all having electrolytes, but with varying amounts of binding agent. In this example, the ingested sports drink will provide electrolytes to the mammal over an extended period of time that may coincide with the period of exercise. In this manner, the sustained-release beads provide electrolytes to the mammal over the entire course of the exercise to replenish electrolytes lost during the period of exercise without requiring the mammal to ingest the sports drink at several instances over the course of the period of exercise.

EXAMPLES

Example 1

Sustained-Release Bead Preparation Method

The following mixture of powders was mixed for 3 minutes in a low shear planetary mixer.
  500 g Caffeine
  300 g Potassium Chloride
  150 g Sodium Chloride
  950 g Microcrystalline cellulose
  100 g Methocel E5
700 kg of water was then added to the powder mixture to produce a wet mass. The wet mass was passed through an LCI extruder at 50 rpm. The extrudate was spheronized in an LCI spheronizer at 1000 rpm for 1 minute to produce spherical beads. The spherical beads had a moisture content of 38.36 wt %. The spherical beads were dried in a Glatt GPCG-3 until the moisture content was reduced to 4.32 wt %. Optionally, the spherical beads were coated with SURLEASE to, a 10% theoretical weight gain and/or OPADRY II to a 4% theoretical weight gain.

Example 2

Dispersion Medium Preparation Method
(Agar-Agar)

2.2 grams of Agar-Agar were combined with 1000 mL of water in a Pyrex glass container. The solution of Agar-Agar and water was then brought to a boil utilizing a heat/stir plate. Boiling continued at 75% heat for 15 minutes or until the Agar-Agar particles completely dissolved in the solution. The water level of the solution was then reconstituted to 1000 mL. The solution was allowed, to cool, followed by the combining 500 mL of the solution with 100 mL of drink syrup concentrate and 100 mL of fructose syrup. The combination, of solution, drink syrup concentrate and fructose syrup was mixed well. Sustained release beads prepared by the method described in Example 1 were then added to the mixture to yield a final bead concentration of 500 mg/500 mL.

Example 3

Dispersion Medium Preparation Method (Xanthan
Gum)

2.4 grams of Xanthan gum were added to the 1000 mL of water. The Xanthan gum and water were mixed in an industrial strength blender on low speed for 60 seconds. The blended solution was transferred to a Pyrex glass container and mixed well with a stir plate. 500 mL of the solution was then combined with 100 mL of drink syrup concentrate and 100 mL of fructose syrup and mixed well. Sustained release beads prepared by the method described in Example 1 were then added to the mixture to yield a final bead concentration of 500 mg/500 mL.

Example 4

Dispersion Medium Preparation Method (Agar-Agat
and Xanthan Gum)

1.5 grams of Agar-Agar were combined with 1000 mL of water in a Pyrex glass container. The solution of Agar-Agar and water was then brought to a boil utilizing a heat/stir plate. Boiling continued at 75% heat for 15 minutes or until the Agar-Agar particles completely dissolved in the solution. The water level of the solution was then reconstituted to 1000 mL. The solution was allowed to cool, followed by the addition of 1.1 grams of Xanthan gum to the Agar-Agar, and water solution. The combined Agar-Agar/Xanthan gum solution was then mixed in an industrial strength blender on low speed for 60 seconds. The blended solution was then transferred to a Pyrex, glass container and mixed with using a stir plate. 500 mL of the blended solution was then combined with 100 mL drink syrup concentrate and 100 mL of fructose syrup. The combination of ingredients was mixed well. Sustained release beads prepared by the method described in Example 1 were then added to the mixture to yield a final bead concentration of 500 mg/500 mL.

As used herein, spatial or directional terms, such as "left," "right," "front," "back," and the like, relate to the subject matter as it is shown in the drawing Figures. However, it is to be understood that the subject matter described herein may assume various alternative orientations and, accordingly, such terms: are not to be considered as limiting. Furthermore, as used herein (i.e., in the claims and the specification), articles such as "the," "a," and "an" can connote the singular or plural. Also, as used herein, the word "or" when used without a preceding "either" (or other similar language indicating that "or" is unequivocally meant to be exclusive—e.g., only one of x or etc.) shall be interpreted to be inclusive (e.g., "x or y" means one or both x or y). Likewise, as used herein, the term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc., used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

In addition, all ranges disclosed herein are to be understood to encompass and provide support for claims that recite any and all subranges or any and all individual values subsumed therein. For example, a stated range of 1 to 10 should be considered to include and provide support for claims that recite, any and all subranges or individual values that are between and/or inclusive of the minimum value of 1 and the maximum value of 10; that is, all subranges beginning, with a minimum, value of 1 or more and ending with a maximum value of 10 or less (e.g., 5.5 to 10, 2.34 to 3.56, and so forth), or any values from 1 to 10 (e.g., 3, 5.8, 9.9994, and so forth).

What is claimed is:

1. A sports beverage comprising:
 a dispersion medium comprising:
  an aqueous solution; and
  a pH modifier; and
 a dispersed phase comprising:
  at least one sustained-release bead comprising:
   at least one binding agent; and
   active ingredients consisting of caffeine, electrolytes, and vitamins.

2. The sports beverage as claimed in claim 1, wherein the at least one binding agent is selected from the group consisting of methyl cellulose, ethyl cellulose, microcrystalline cellulose, croscarmellose sodium, dicalcium phosphate, cellulose, hypromellose, hydroxypropyl methylcellulose, carboxymethylcellulose, and hydroxyethyl cellulose.

3. The sports beverage as claimed in claim 1, wherein a total amount of the binding agent in each of the at least one sustained-release bead of the dispersed phase ranges from 40 wt % to 95 wt % of the sustained-release bead.

4. The sports beverage as claimed in claim 1, wherein the pH modifier is selected from the group consisting of citric acid, phosphoric acid, sodium citrate, potassium citrate, ascorbic acid, benzoic acid, malic acid, lactic acid, fumaric acid, and combinations thereof.

5. The sports beverage as claimed in claim 1, wherein the at least one sustained-release bead further comprises:
 a cellulose-based coating.

6. The sports beverage as claimed in claim 1, wherein the aqueous solution comprises water.

7. The sports beverage as claimed in claim 1, wherein the sports beverage includes only ingredients that are GRAS-compliant or present in GRAS-compliant quantities.

8. The sports beverage of claim 1, wherein the diameter of each of the at least one sustained-release bead has a diameter in the range of 0.5 mm to 5.0 mm.

9. The sports beverage of claim 1, wherein each of the at least one sustained-release bead is an uncoated sustained-release bead.

10. The sports beverage of claim 1, wherein a total amount of the binding agent in each of the at least one sustained-release bead is about 50 wt % of the sustained-release bead.

11. The sports beverage of claim 1, wherein the dispersion medium has a pH in the range of from 2.0 to 3.5.

12. The sports beverage of claim 1, wherein each of the at least one sustained-release bead does not dissolve in the dispersion medium.

* * * * *